United States Patent [19]

Baker, Jr. et al.

[11] Patent Number: 4,624,260
[45] Date of Patent: Nov. 25, 1986

[54] PACEMAKER WITH CONDITIONAL ATRIAL TRACKING CAPABILITY

[75] Inventors: Ross G. Baker, Jr.; Richard V. Calfee; Richard S. Sanders, all of Houston; Joe Vandegriff, Freeport, all of Tex.; Jay Warren, Placerville, Calif.

[73] Assignee: Intermedics, Inc., Angleton, Tex.

[21] Appl. No.: 731,581

[22] Filed: May 7, 1985

[51] Int. Cl.$^4$ .............................................. A61N 1/36
[52] U.S. Cl. ............................................. 128/419 PG
[58] Field of Search ................................ 128/419 PG

[56] References Cited

U.S. PATENT DOCUMENTS

| | | | |
|---|---|---|---|
| 4,163,451 | 8/1979 | Lesnick et al. | 128/419 PG |
| 4,280,502 | 7/1981 | Baker, Jr. et al. | 128/419 PG |
| 4,312,355 | 1/1982 | Funke | 128/419 PG |
| 4,335,727 | 6/1982 | McPherson | 128/419 PG |
| 4,386,610 | 6/1983 | Leckrone | 128/419 PG |
| 4,467,810 | 8/1984 | Vollmann | 128/419 PG |
| 4,554,920 | 11/1985 | Baker, Jr. et al. | 128/419 PG |
| 4,572,192 | 2/1986 | Jackman et al. | 128/419 PG |
| 4,572,193 | 2/1986 | Mann et al. | 128/419 PG |
| 4,577,634 | 3/1986 | Gessman | 128/419 PG |

*Primary Examiner*—William E. Kamm
*Assistant Examiner*—Mitchell J. Shein
*Attorney, Agent, or Firm*—Willian Brinks Olds Hofer Gilson & Lione, Ltd.

[57] ABSTRACT

An implantable microprocessor-controlled dual chamber heart pacemaker is programmed to control the timing of the pacing of the ventricle in response to high rate atrial signals. The microprocessor operates in conjunction with an atrial timer to detect atrial signals which occur at a rate in excess of a predefined atrial rate limit. The microprocessor paces the ventricle at a predefined desirable demand rate and inhibits pacing of the atrium in response to the high rate atrial activity. The microprocessor also controls the timing of an atrial refractory interval which includes an absolute refractory portion during which atrial signals are not detected and a relative refractory portion during which atrial signals are detected but are not tracked. The combined absolute and relative atrial refractory portions insure that relatively high rate atrial signals are detected and spurious signals conducted from the ventricle are ignored.

21 Claims, 8 Drawing Figures

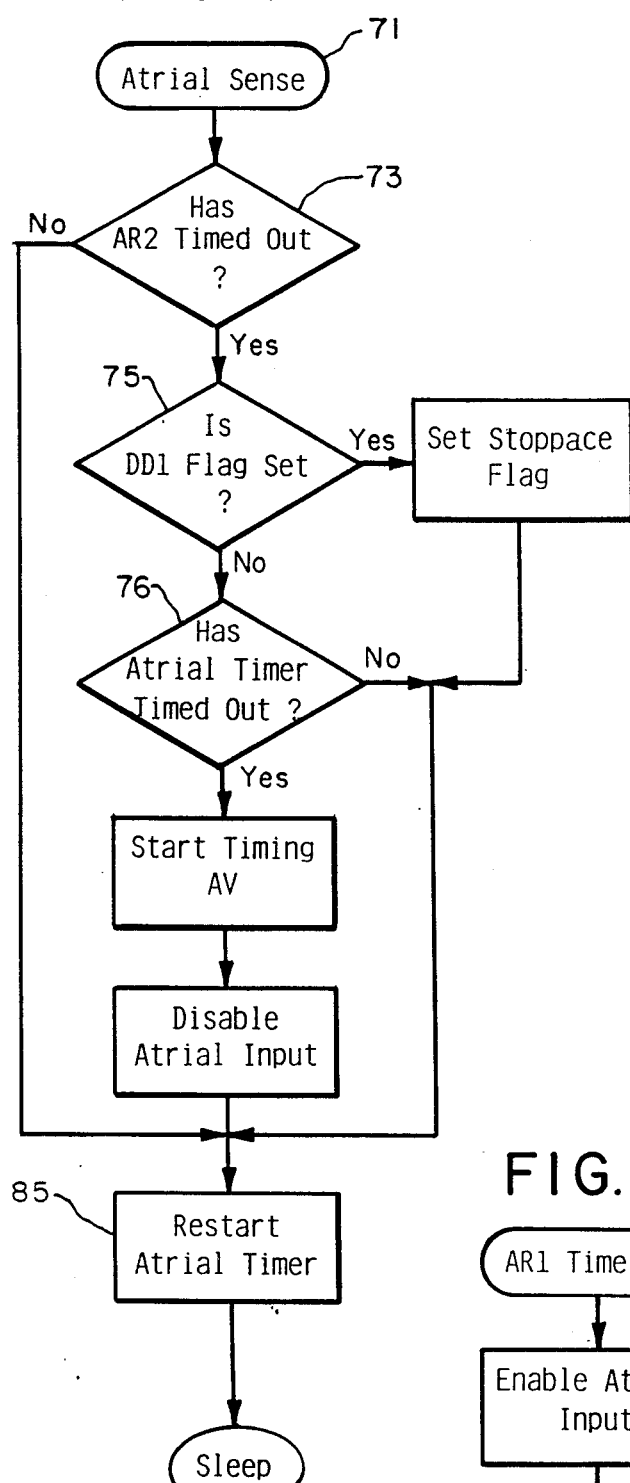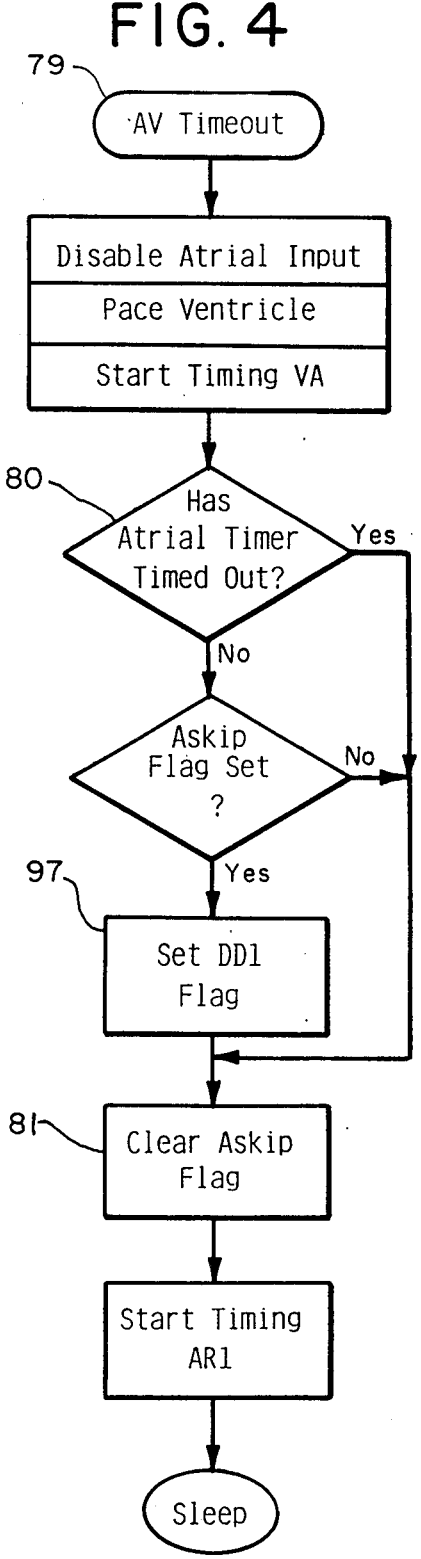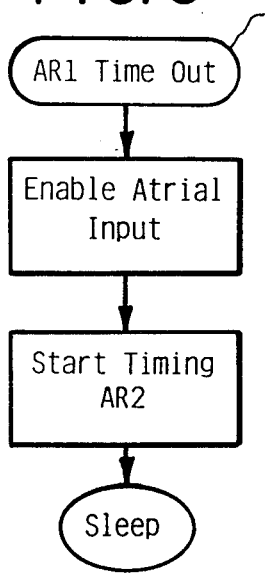

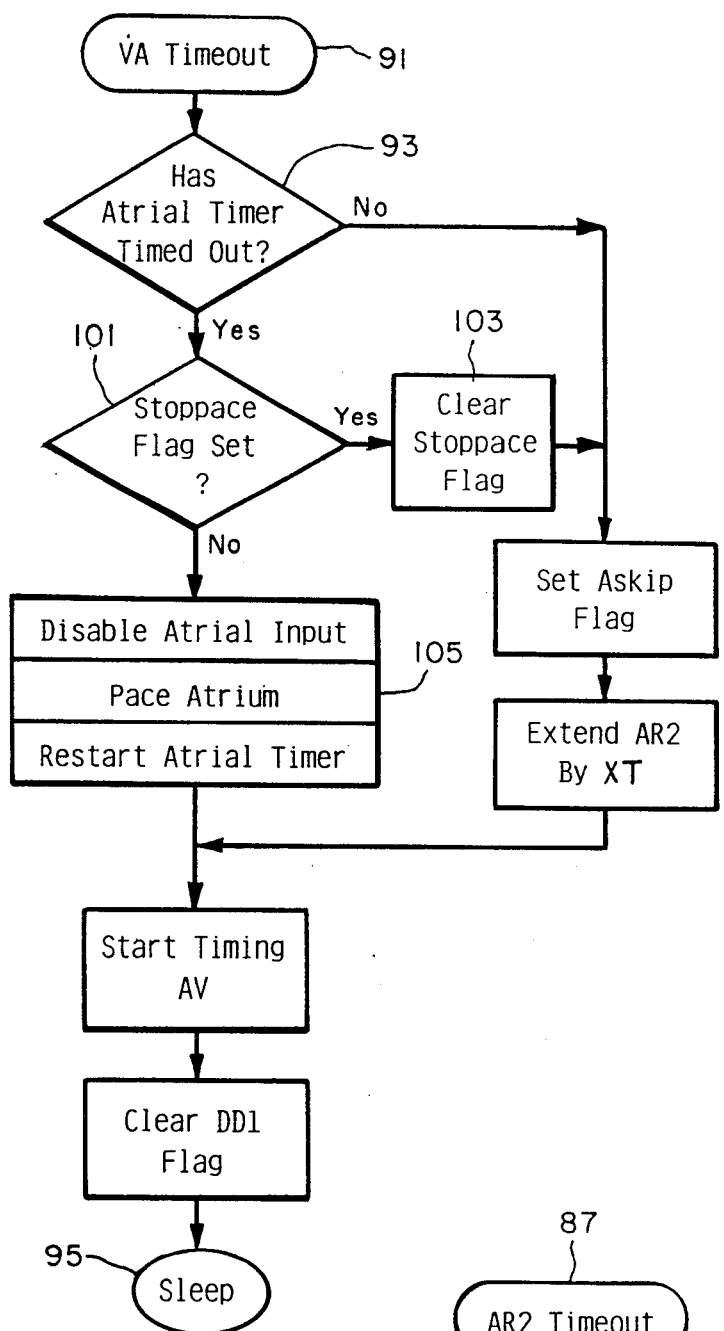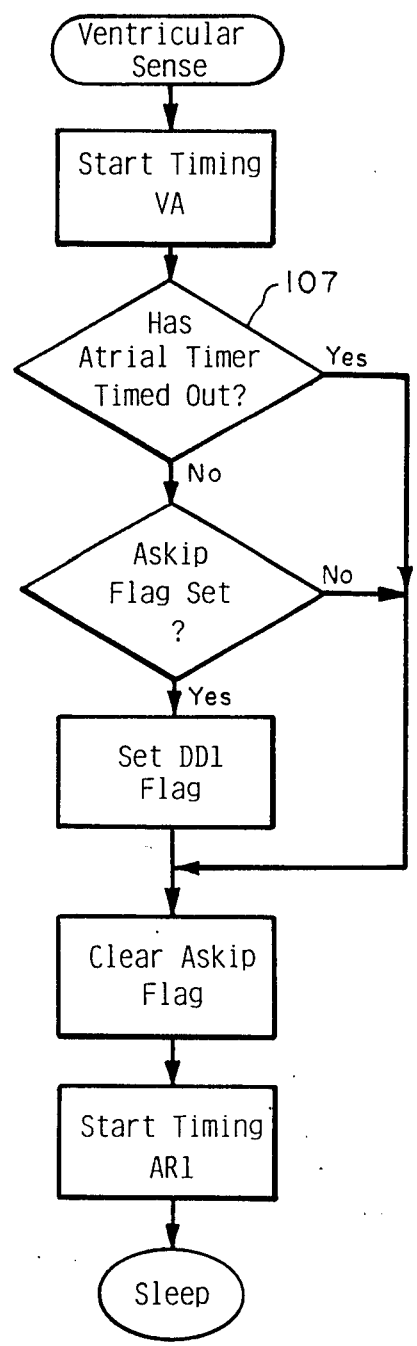

PACEMAKER WITH CONDITIONAL ATRIAL TRACKING CAPABILITY

TECHNICAL FIELD

The invention relates to body implantable pacemakers which monitor electrical activity in the atrium and ventricle of the heart and stimulate heart tissue as required to maintain the proper operation of the heart. More particularly, the invention relates to a dual chamber pacemaker which ignores atrial signals occurring at a rate in excess of a preselected upper rate limit and paces the ventricle at a preselected desirable lower demand rate.

BACKGROUND OF THE INVENTION

Dual chamber pacemakers sense electrical P-waves which occur in the atrium of the heart and pace the ventricle in synchronism with these signals in the absence of corresponding natural ventricular R-wave signals. In operation, an electrode disposed in the atrium detects a P-wave and, in the absence of corresponding ventricular activity, applies a delayed, synchronized electrical signal to cause the ventricle to contract. The dual chamber pacemaker thus "tracks" atrial signals by applying corresponding pacing signals to the ventricle.

Atrial P-waves having a relatively high rate will cause a dual chamber pacemaker to stimulate the ventricle at a corresponding high rate. As a matter of safety, it has been suggested that such pacemakers should pace the ventricle in response to high rate atrial events up to a defined ventricular rate limit, in order to avoid overstimulating the ventricle.

In order to avoid prolonged pacing at the ventricular rate limit, it has been suggested that the rate of pacing of the ventricle may be gradually reduced from the ventricular rate limit in a programmed manner to a predetermined lower pacing rate. Alternatively, the average pacing rate of the ventricle could be reduced in accordance with known operation of the pacemaker in a Wenckebach manner.

The known methods of pacing the ventricle in response to high rate atrial signals require that the pacemaker track the atrial signals and pace the ventricle at an increased rate. This operation is particularly undesirable if the high rate atrial signals which are being tracked are generated by a non-physiological source, for example a microwave transmitter. Even if the high rate atrial activity is physiological in origin, as in an atrial tachycardia, it may not be desirable to pace the ventricle of a diseased heart at a corresponding high rate.

It is therefore desirable to provide a pacemaker which will detect and ignore atrial activity above a predefined rate and which will pace the ventricle at a desirable lower rate and will inhibit pacing of the atrium in the presence of such atrial activity.

It is another object of the invention to provide a pacemaker which will track atrial signals occurring at a rate less than a selected atrial rate limit and which will pace the heart in a demand fashion at a desirable lower ventricular pacing rate if atrial signals occur at or above the atrial rate limit.

It is a further object of the invention to provide such a pacemaker with an atrial timer for detecting high rate atrial signals and a microprocessor control for pacing the ventricle at a predetermined preferred rate in response to the detection of the high rate atrial signals.

It is another object of the invention to provide a software-controlled pacemaker which detects high rate atrial events and prevents pacing of the atrium when such events are detected.

Conventional pacemakers use an atrial refractory interval following a paced or sensed ventricular event to avoid tracking spurious signals conducted from the ventricle to the atrium. Such atrial refractory intervals are usually "absolute" in the sense that atrial signals cannot be detected over the entire interval. The absolute refractory interval has the advantage of preventing the detection of spurious signals conducted from the ventricle, but it can also mask real atrial signals and thus unnecessarily inhibit tracking of these signals. Reducing the duration of the absolute atrial refractory interval has the desirable effect of increasing the chance of detecting real high rate atrial signals and the undesirable effect of increasing the risk of detecting spurious signals from the ventricle.

It is therefore desirable to reduce the duration of the absolute atrial refractory interval of a dual chamber pacemaker without also increasing the risk of tracking spurious signals from the ventricle.

Accordingly, it is an object of the invention to provide a pacemaker which facilitates tracking of high rate atrial events by using an atrial refractory interval following a paced or sensed ventricular event which includes an absolute refractory subinterval during which atrial events are not detected and a relative refractory subinterval during which atrial events are detected but are not tracked.

SUMMARY OF THE INVENTION

In order to achieve the objects of the invention and to overcome the problems of the prior art, the pacemaker of the invention includes a microprocessor which is programmed to control the timing of the pacing of the ventricle and atrium. The microprocessor operates in conjunction with an atrial timer to detect atrial events which occur at a rate in excess of a predefined atrial rate limit. The microprocessor paces the ventricle at a predefined desirable demand rate and inhibits pacing of the atrium in response to the high rate atrial activity. The microprocessor also controls the timing of an atrial refractory interval which includes an absolute refractory portion during which atrial signals are not detected and a relative refractory portion during which atrial signals are detected but are not tracked.

BRIEF DESCRIPTION OF THE DRAWINGS

FIGS. 3-8 are flow charts of a software system for operating a microprocessor controlled pacemaker to achieve the objects of the invention.

DETAILED DESCRIPTION OF PREFERRED EMBODIMENT

Figure 1:
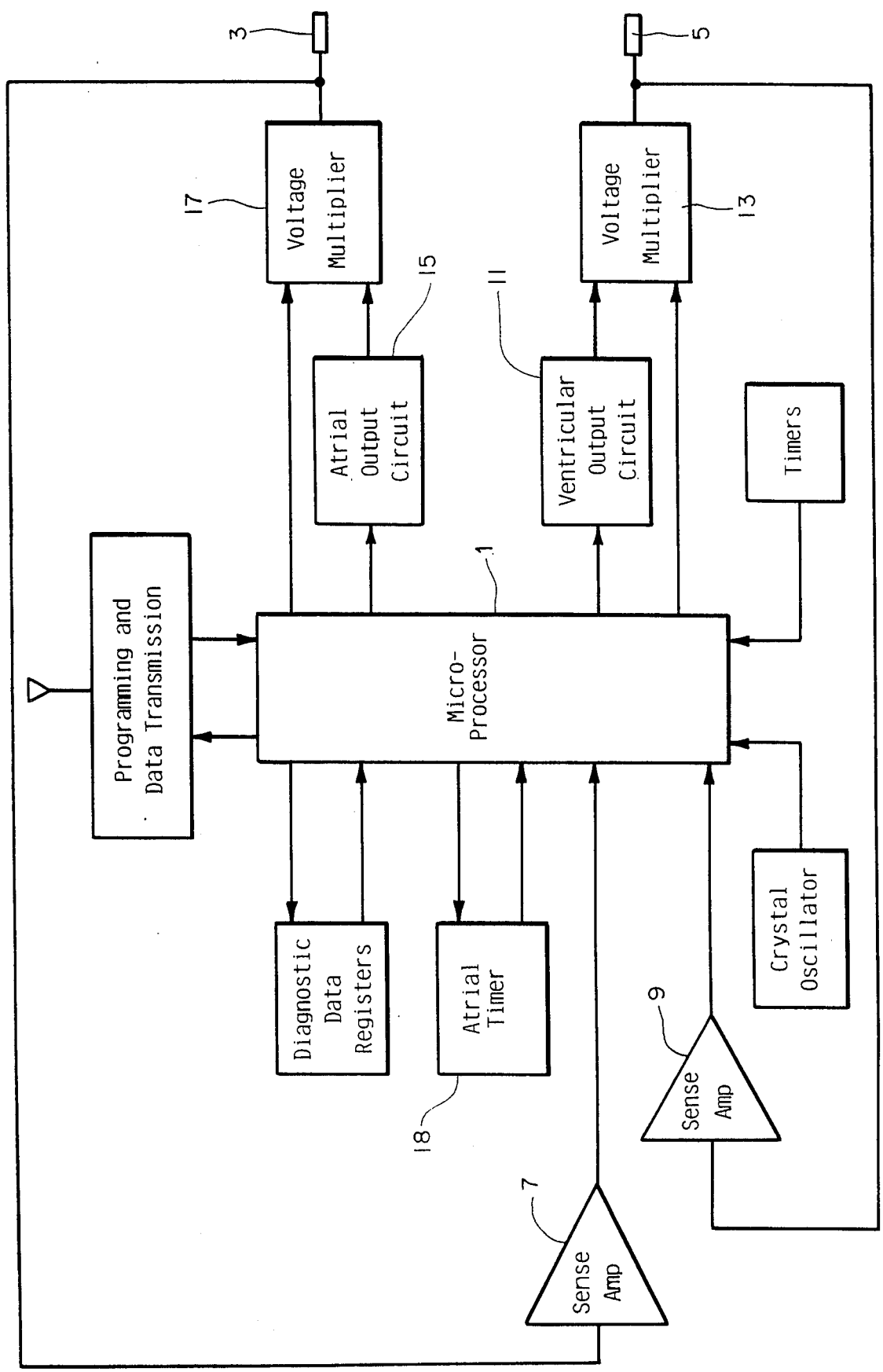
FIG. 1 illustrates a block diagram of the primary components of the cardiac pacemaker of the invention.

The remaining portion of the specification will describe a preferred embodiment of the invention when read in conjunction with the attached drawings, in which like reference characters identify identical apparatus.

FIG. 1 illustrates a block diagram of the major components of a preferred embodiment of the pacemaker of the invention. As shown in FIG. 1, the pacemaker includes a microprocessor 1 which is programmed to apply atrial and ventricular pacing pulses to the heart in accordance with sensed atrial and ventricular conditions. In operation, an atrial electrode 3 of a unipolar or bipolar type, and a ventricular electrode 5 of a unipolar or bipolar type are respectively connected to the atrium and ventricle of the heart in a manner known to the art. Signals are sensed by the electrodes 3 and 5 and are applied to respective sense amplifiers 7 and 9 which then transmit amplified signals to the microprocessor 1.

In particular modes of operation, for example, the VDD mode and DDD mode, the microprocessor 1 is operated to monitor electrical signals of the atrium and ventricle. In operation, the pacemaker defines a VA interval which extends for a predefined time following a sensed or paced ventricular event. The pacemaker further defines an AV interval which extends for a predefined time following a sensed or paced atrial event in the DDD mode. In the VDD mode, the AV interval is timed at the end of a ventricular pacing interval corresponding to the VA interval. In the VDD and DDD modes, the microprocessor 1 operates a ventricular output circuit 11 and a corresponding voltage multiplier 13 to pace the ventricle over the lead 5. The ventricle is paced at the end of the AV interval if a ventricular event is not sensed within the interval. If a ventricular event is sensed within the interval, the ventricle is not paced at the end of the AV interval.

In the DDD mode, an atrial output circuit 15 is operated in conjunction with an associated voltage multiplier 17 to pace the atrium over the atrial electrode 3. In general operation, the atrium is paced if a natural atrial event is not sensed within the VA interval following pacing or sensing in the ventricle. If an atrial event is sensed within the interval, the atrium is not paced.

In both the DDD and VDD modes, atrial refractory intervals are provided for a time following a sensed atrial event and for a time following a sensed or paced ventricular event. In general, atrial events that occur within the atrial refractory intervals will be ignored by the pacer. Likewise, a ventricular refractory period is defined following a sensed or paced ventricular event. The pacer will ignore any signals detected within this ventricular refractory period.

The pacer system of FIG. 1 is capable of operating in modes other than the VDD or DDD modes. However, the VDD and DDD modes of operation are of particular interest with respect to the invention and therefore the operation of the pacing system of the invention will be described hereafter with respect to these modes.

The above-described general operation of a software-controlled dual chamber pacemaker and the background of the invention may be understood by reference to allowed application Ser. No. 443,830, now U.S. Pat. No. 4,554,920, entitled Microprocessor Controlled Cardiac Pacemaker and Method For Avoiding Pacer Sustained Tachycardia, filed Nov. 22, 1982, and assigned to the assignee of the present patent application. The disclosure of application Ser. No. 443,830 is incorporated herein by reference.

Figure 2:
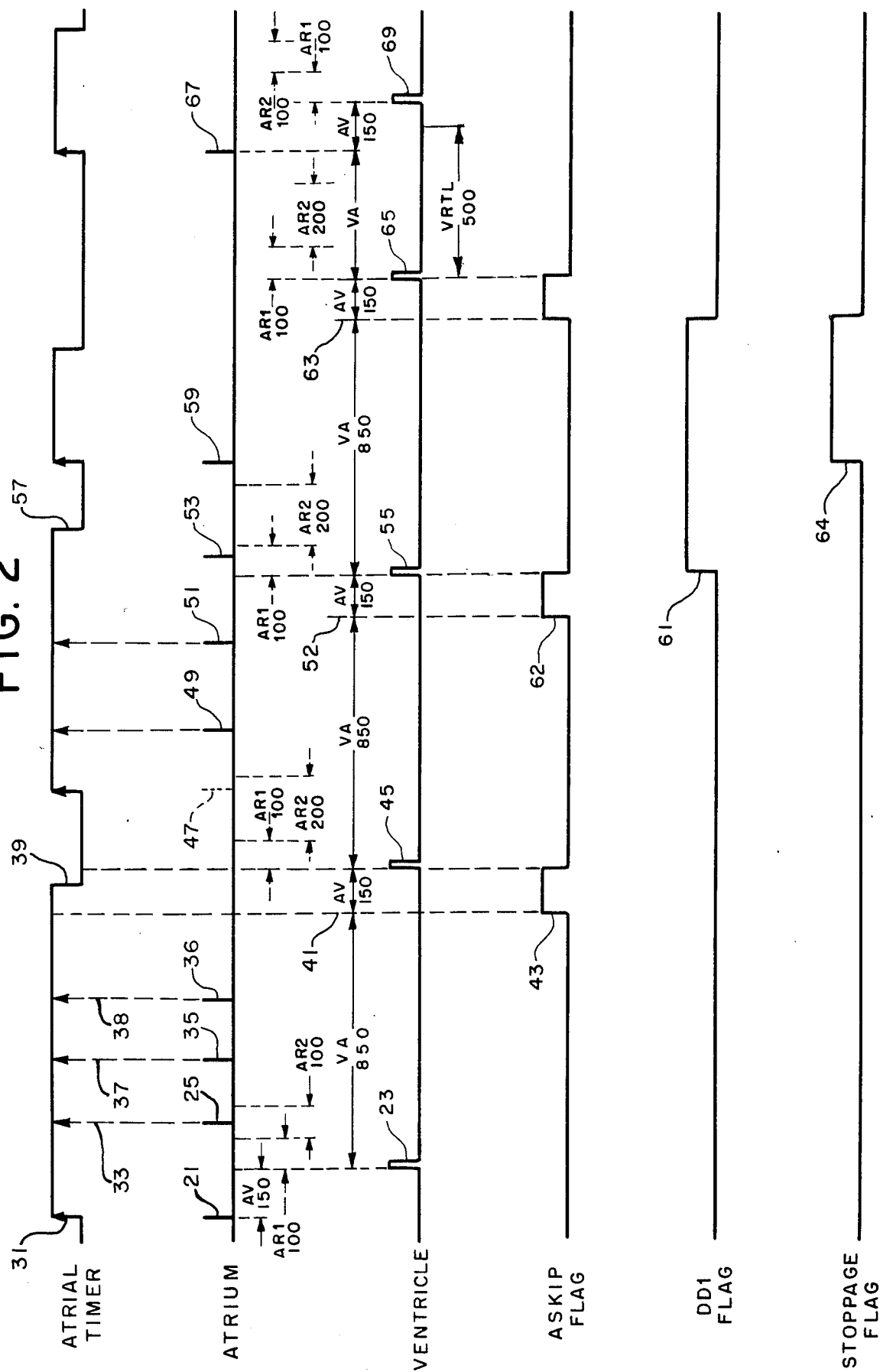
FIG. 2 illustrates a diagram of atrial and ventricular signals and associated timing signals which occur in the pacemaker of the invention.

FIG. 2 illustrates a timing diagram of electrical signals in the atrium and ventricle and corresponding timing signals which occur in the system of FIG. 1 in accordance with the invention. In the discussion of the timing diagram of FIG. 2, it shall be assumed that a natural P-wave signal 21 is initially detected by the pacemaker and the ventricle is then paced at 23 after an AV delay of, for example, 150 milliseconds. Pacing of the ventricle in response to an atrial signal shall hereafter be referred to as "tracking" the atrial signal. Thus, with reference to FIG. 2, the pacemaker of the invention tracks the atrial signal 21 by pacing the ventricle at 23. It should generally be understood that periods in milliseconds are provided in the timing diagram of FIG. 2 to facilitate an understanding of the invention. These periods are specified only to aid in explaining the invention and are not intended to limit the scope of the invention.

Following pacing of the ventricle at 23, the pacemaker times out a programmed VA interval of for example 850 milliseconds and programmed atrial refractory intervals AR1 and AR2. The interval AR1 is an absolute atrial refractory interval during which the output of the atrial amplifier 7 is ignored by the microprocessor so that atrial signals cannot be detected following pacing of the ventricle or sensing of a ventricular event. This absolute atrial refractory interval is required in order to avoid sensing a conducted ventricular signal in the atrium. AR2 is a relative atrial refractory interval during which atrial events are detected but are not tracked. That is, atrial events detected during the interval AR2 do not initiate pacing of the ventricle.

In the system of the invention, the duration of the absolute atrial refractory interval AR1 is sufficiently long to allow the pacemaker to ignore spurious signals conducted from the ventricle and is sufficiently short to allow the pacemaker to detect real atrial signals having a relatively high rate. The relative atrial refractory interval AR2 is provided to avoid tracking atrial signals which occur too soon following pacing or sensing in the ventricle but which must be detected to properly monitor the rate of real atrial activity. It has been found that intervals of 100 milliseconds for AR1 and AR2 may be advantageously employed in the system of the invention. However, other durations could be employed to increase the chance of detecting high rate atrial activity and reduce the risk of detecting spurious signals conducted from the ventricle.

As shown in FIG. 1, in the system of the invention, an atrial timer 18 times an atrial rate limit interval following each detected atrial signal. For illustrative purposes, it shall hereafter be assumed that the pacemaker of the invention is programmed with an atrial rate limit of 150 beats per minute. This pacing rate corresponds to an atrial timer interval of 400 milliseconds. Thus, atrial signals occurring at intervals less than 400 milliseconds will exceed the predefined atrial rate limit. The suggested atrial rate limit is provided for illustrative purposes and is not intended to limit the scope of the invention.

As shown in FIG. 2, the atrial signal 21 initiates (at 31) timing of the 400 millisecond atrial rate limit interval by the atrial timer 18. A subsequent atrial signal 25 occurs approximately 300 milliseconds following the signal 21 and therefore falls within the atrial rate limit interval of 400 milliseconds. The atrial timer 18 is restarted by the atrial signal 25 to begin retiming the 400 millisecond interval at 33. Thereafter atrial signals 35 and 36 occur at intervals of 200 milliseconds following the atrial signal 25 and again restart the atrial timer at 37 and 38 respectively. The timer then times out its 400 millisecond interval at 39 in the absence of further atrial activity.

The pacemaker of the invention will not track atrial signals which occur at a rate above the predefined atrial rate limit. The pacemaker thus does not track atrial signals which occur when the atrial timer is timing out. Accordingly, the atrial signals 25, 35 and 36 do not initiate a pace of the ventricle, because they occur while the atrial timer is timing out.

The pacemaker of the invention thus ignores the atrial signals 25, 35 and 36 and times out the preprogrammed refractory intervals AR1 and AR2 following the pace of the ventricle at 23. After timing the refractory intervals, the pacemaker continues to time the VA interval, because the atrial signals 25, 35 and 36 do not initiate a pace of the ventricle. When the VA interval times out at 41, the microprocessor 1 interrogates the atrial timer 18 to determine if it is still timing out. As shown in FIG. 2, at the point 41 at which the VA interval ends, the atrial timer is still timing. Thus, the microprocessor is informed that a high rate atrial event has recently occurred and it is therefore undesirable to pace the atrium. The microprocessor therefore sets an ASKIP flag at 43, adds an extension XT of, for example, 100 milliseconds to the duration of the relative refractory interval AR2 of the next cycle and times out the VA interval at 41 but does not pace the atrium. Thereafter, an AV interval of for example 150 milliseconds is timed, the ventricle is paced at 45 in the absence of a natural ventricular event and the ASKIP flag is cleared. The high rate atrial activity therefore causes the ventricle to be paced at a relatively low predefined rate of 60 beats per minute (1000 millisecond interval).

It should be understood that if the high rate atrial signal 36 had not occurred, the atrial timer would have timed out before the end of the VA interval and the atrium would have been paced at 41. Alternatively, if the signal 36 had occurred slightly more than 400 milliseconds following the signal 35, the microprocessor would interrupt timing of the VA interval and would initiate timing of the AV interval. The microprocessor would thereafter pace the ventricle at the end of the AV interval or following timeout of a ventricular rate limit interval VRTL, whichever is longer, unless a ventricular signal is detected while the AV and ventricular rate limit intervals are being timed.

Following the ventricular pace at 45 the AR1 interval, extended AR2 interval and VA interval are timed. The relative atrial refractory interval AR2 was extended in the previous timing cycle in order to avoid a pacemaker sustained tachycardia wherein the pacemaker paces the ventricle at an undesirably high rate by tracking spurious signals passed to the atrium by retrograde conduction from the ventricle. Retrograde conduction of the ventricular pace signal 45 can occur because a preceding pace of the atrium was inhibited at 41 and the tissue connecting the atrium and ventricle could therefore be conductive. A pacemaker sustained tachycardia is avoided because the spurious retrograde conducted atrial signal 47 falls within the extended relative atrial refractory interval AR2 and is therefore not tracked by the pacemaker. In operation, a pacemaker sustained tachycardia is avoided by extending the AR2 interval for the cycle following each inhibition of an atrial pace.

The signal 47 starts the atrial timer 18 and the timer is thereafter restarted by succeeding atrial signals 49 and 51 which occur at intervals less than the 400 millisecond interval for the atrial rate limit. The pacemaker does not track the atrial signals 49 and 51, because they occur while the atrial timer is timing out.

The ASKIP flag is set at 62 when the VA interval times out, because the atrial timer is still timing its interval as a result of the occurrence of the high rate atrial signal 51. Accordingly, the pacemaker does not pace the atrium at the end 52 of the VA interval. Also, the AV interval is timed following the end 52 of VA, the ventricle is paced at 55 and the ASKIP flag is cleared when the ventricle is paced.

It will be noted that an atrial signal 53 occurs during the absolute atrial refractory interval AR1 following the pace of the ventricle at 55. As previously described, an atrial signal falling within the interval AR1 will not be detected by the pacemaker. Thus, the signal 53 does not clear the atrial timer 18 and therefore the timer times out at 57, 400 milliseconds following the previously detected atrial signal 51.

As a result of the occurrence of the atrial signal 53 in the interval AR1, a following high rate atrial event 59 will occur at a time when the atrial timer is not timing its interval. Thus, the pacemaker cannot recognize the atrial signal 59 as a high rate signal by reference to the atrial timer in the manner previously described.

The pacemaker recognizes the signal 59 may be a high rate signal and thus does not track the signal as a result of the setting of a DDI flag at the time of the ventricular pace 55. The DDI flag is set when the ASKIP flag has been set, the atrial timer 18 is timing its interval and a signal is sensed in the ventricle or the ventricle is paced. Thus, with reference to FIG. 2, the DDI flag is set at 61 in response to the timing of the atrial timer, the setting of the ASKIP flag at 62 and the pacing of the ventricle at 55.

When the atrial signal 59 occurs during the VA interval, the pacemaker interrogates the DDI flag and sets a STOPPACE flag at 64. The STOPPACE flag is thus set when the DDI flag has been set and an atrial signal is detected during the VA interval.

The set condition of the DDI flag tells the microprocessor 1 not to track atrial signals in the present timing cycle because an atrial pace was inhibited in the previous cycle as a result of high rate atrial activity and such activity is likely to continue in the present cycle. The set condition of the STOPPACE flag tells the microprocessor that atrial activity is continuing during the present cycle with the DDI flag set and therefore the atrium should not be paced in the present cycle. The DDI and STOPPACE flags are thus employed by the microprocessor to operate the pacemaker in the DDI mode for one cycle.

It should be understood that, if the atrial signal 59 had not occurred, STOPPACE would have remained in its cleared state. If STOPPACE thus remained clear, the atrium would be paced at 63.

Following the timing out of the VA interval at 63 the DDI and STOPPACE flags are cleared, the ASKIP flag is set to indicate that a pace of the atrium has been skipped, an AV interval is timed, the ventricle is paced at 65 and the ASKIP flag is cleared. Thereafter the AR1 interval and the extended relative refractory interval AR2 are timed. The AR2 interval is extended in this instance because an atrial pace was skipped at 63 in the previous cycle.

After all flags are cleared and the atrial timer has timed out, it is assumed that atrial signal 67 occurs. The pacemaker will track this signal by timing an AV interval and pacing the ventricle at 69, since the ventricular rate limit VRTL of, for example 500 milliseconds, has timed out. Thereafter the AR1 interval and nonextended AR2 interval are timed.

It should be understood from the timing diagram of FIG. 2 that the pacemaker of the invention can be programmed to pace the ventricle at a safe relatively low demand rate of, for example, 60 beats per minute in the presence of atrial signals which occur at a rate exceeding the atrial rate limit of 150 beats per minute. The pacemaker thus in effect ignores high rate atrial signals and paces the ventricle at a preselected safe demand rate. When the atrial rate drops to a lower value, for example a rate below 150 beats per minute, the pacemaker again tracks atrial signals and paces the ventricle in synchronism with the signals.

It should be understood that the pacemaker of the invention utilizes the atrial timer 18 to detect high rate atrial signals and to prevent the pacer from tracking such signals. The ASKIP flag is used to indicate that a pace of the atrium has been skipped during a cycle in which high rate atrial events have been detected. A DDI flag is used to avoid tracking atrial signals which occur in a cycle following a previous cycle in which high rate atrial signals are detected, if the ventricular pace or sense event of the previous cycle occurred when the atrial timer was timing its interval. The STOPPACE flag is employed to prevent the pacemaker from pacing the atrium when at least one atrial signal is detected during the VA interval in a cycle during which the DDI flag is set.

In the system of the invention the pacemaker operates in a VVI-like mode to avoid tracking and pacing the atrium in the presence of high rate atrial activity. The pacemaker is further operated in the DDI mode to prevent tracking of atrial signals under the above-described conditions wherein the DDI flag is set. The pacemaker of the invention is therefore advantageously switched in its apparent modes of operation to achieve the objects of the invention.

It should be appreciated that natural ventricular signals have not been included in the timing diagram of FIG. 2 in order to facilitate an understanding of the invention. However, it should be understood that sensed natural ventricular signals will reset the ASKIP flag, set the DDI flag, and start timing of the atrial refractory intervals in the manner described for the ventricular pace signals of FIG. 2.

FIGS. 3–8 illustrate the flow charts of a computer program for operating the microprocessor 1 to achieve the objects of the invention.

The microprocessor 1 has an active state during which it performs computational or logic functions and an inactive or sleep state wherein its logic functions are suspended while it waits for an interrupt condition or for a timer to time out. The flow charts of FIGS. 3–8 will hereafter be discussed with respect to the operation of the microprocessor in its active and sleep states. The logic flow of the computer program will be discussed with respect to the timing diagram of FIG. 2.

When the atrial signal 21 of FIG. 2 is sensed, the microprocessor wakes up at point 71 of FIG. 3 and determines at 73 that the relative atrial refractory interval AR2 has timed out. The microprocessor then interrogates the DDI Flag at point 75 and determines that the flag has not been set. Thereafter the atrial timer 18 is checked at point 76 to determine if it has completed timing its atrial rate limit interval. In this case the timer has timed out and therefore the microprocessor sets a timer to begin timing the AV interval, disables its input from the atrial amplifier 7, restarts the atrial timer 18 and then goes to sleep to await the timing out of the AV interval.

When the AV interval times out, the microprocessor wakes up at point 79 of FIG. 4, again disables its input from the atrial amplifier 7, paces the ventricle as shown at 23 of FIG. 2 and sets a timer to begin timing the VA interval. With reference to FIG. 4, the microprocessor thereafter interrogates the atrial timer at 80 and determines that it is still timing its atrial rate limit interval. The microprocessor therefore clears the ASKIP flag at 81. In this case the flag is unaffected, since it has already been cleared. The microprocessor then sets a timer to start timing the absolute atrial refractory interval AR1 and returns to its sleep state.

With reference to FIG. 5, when the AR1 interval times out, the microprocessor wakes up at 83 and enables its input from the atrial amplifier 7. Thereafter the microprocessor sets a timer to time the relative atrial refractory interval AR2 and goes back to sleep. The AR2 interval is set at this point to its nominal value of 100 milliseconds, because there was no immediately preceding inhibition of a pace of the atrium as a result of high rate atrial activity.

As shown in FIG. 2, the high rate atrial signal 25 is the next event which occurs. With reference to FIG. 3, the microprocessor wakes up at 71 when the signal 25 is sensed and determines at 73 that the AR2 interval has not timed out. Under this circumstance, the microprocessor restarts the atrial timer 18 at 85 and then goes back to sleep to await a time out of the AR2 interval.

With reference to FIG. 6, when AR2 times out, the microprocessor wakes up at 87, resets AR2 to its nominal value and then goes to sleep at 89.

When the next atrial signal 35 is detected, the microprocessor wakes up at 71 of FIG. 3 and determines that the AR2 interval has timed out, the DDI flag is not set and the atrial timer has not completed timing its interval. The atrial timer is therefore restarted at 37 of FIG. 2. The microprocessor then goes back to sleep to await timing out of the VA interval. The same program steps are repeated for the atrial signal 36.

With reference to FIG. 2, when the VA interval times out at 41, the microprocessor wakes up at point 91 of FIG. 7 and determines at 93 that the atrial timer has not timed out. The microprocessor therefore sets the ASKIP flag as indicated at point 43 of FIG. 2 and extends the nominal value of the AR2 interval by XT. The atrium is not paced because the atrial timer was timing out at the end of the VA interval. Thereafter the microprocessor sets a timer to begin timing the AV interval, clears the previously cleared DDI flag and goes to sleep at 95. The input from the atrial amplifier is not disabled because an atrial pace following the VA interval has been skipped.

With reference to FIG. 4, when the AV interval times out, the microprocessor wakes up at 79, disables its input from the atrial amplifier 7, paces the ventricle as indicated at point 45 of FIG. 2 and sets a timer to start timing the VA interval. After pacing the ventricle the microprocessor determines at 80 that the atrial timer has timed out and therefore clears the ASKIP flag at 81 and sets a timer to begin timing the atrial refractory interval AR1. The microprocessor then goes to sleep.

Thereafter the microprocessor operates in the manner previously described with respect to FIG. 5 in starting timing of the AR2 interval. It should be recalled that the AR2 interval was previously extended and therefore the timer begins timing out the extended interval. The microprocessor goes to sleep and thereafter wakes up when the retrograde signal 47 of FIG. 2 is detected while AR2 is timing out.

With reference to FIG. 3, sensing of the signal 47 wakes up the microprocessor at 71. Since AR2 has not timed out, the microprocessor restarts the atrial timer at 85 and then goes to sleep.

When the extended AR2 interval times out, the microprocessor wakes up at point 87 of FIG. 6, resets AR2 to its nominal value and returns to sleep at 89.

While the VA interval is timed, the atrial signals 49 and 51 are each detected and the microprocessor is awakened in each case at 71 of FIG. 3 as previously described. In each case the microprocessor determines that the AR2 interval has timed out, the DDI flag is not set and the atrial timer has not completed timing its interval. Program control is therefore transferred in each case to the point 85 to restart the atrial timer. After the second of the atrial signals 51, the microprocessor returns to its sleep state to await timing out of the VA interval.

With reference to FIG. 7, the microprocessor wakes up at point 91 when the VA interval times out and determines at 93 that the atrial timer has not timed out. The ASKIP flag is then set as shown at point 62 of FIG. 2 and the value of the relative atrial refractory interval AR2 is extended to reflect the fact that an atrial pace has been skipped. The microprocessor then sets a timer to begin timing the AV interval, again clears the DDI flag and goes to sleep at 95.

With reference to FIG. 4, the microprocessor wakes up at point 79 when the AV interval times out, disables its input from the atrial amplifier 7, paces the ventricle at the point 55 of FIG. 2 and sets a timer to begin timing the VA interval. With reference to FIG. 4, the microprocessor then determines that the atrial timer has not timed out and the ASKIP flag is set. The microprocessor therefore sets the DDI flag at 97, as indicated at 61 of FIG. 2. Thereafter the ASKIP flag is cleared, a timer is set to begin timing the AR1 interval and the microprocessor goes to sleep to await timing out of the AR1 interval.

It should be understood that the atrial signal 53 of FIG. 2 occurs during the absolute atrial refractory interval AR1 and is therefore not detected by the pacemaker. Accordingly, the microprocessor remains asleep until the interval AR1 times out. As previously discussed with respect to FIG. 5, when AR1 times out the microprocessor wakes up and, after enabling the input from the atrial amplifier, sets a timer to begin timing the extended AR2 interval. The microprocessor then goes to sleep and, when AR2 times out, wakes up at 87 of FIG. 6, resets AR2 to its nominal value and then goes to sleep at 89.

When the atrial signal 59 of FIG. 2 is detected, the microprocessor wakes up at point 71 of FIG. 3 and determines that the AR2 interval has timed out and the DDI flag has been set. The microprocessor therefore sets the STOPPACE flag as shown at 64 of FIG. 2, restarts the atrial timer and goes to sleep to await timing out of the VA interval.

When the VA interval times out, the microprocessor wakes up at point 91 of FIG. 7, determines at 93 that the atrial timer has timed out its interval and interrogates the condition of the STOPPACE flag at 101. Since the STOPPACE flag is set, the microprocessor clears the STOPPACE flag at 103, sets the ASKIP flag and extends the value of the AR2 interval to reflect the fact that an atrial pace has been skipped. Thereafter the microprocessor sets a timer to begin timing the AV interval, clears the DDI flag and goes to sleep at 95.

The microprocessor wakes up at 79 of FIG. 4 when the AV interval times out and thereafter disables the inputs of the atrial amplifier 7 and paces the ventricle, as shown at 65 of FIG. 2. The microprocessor then determines that the atrial timer has timed out and therefore clears the ASKIP flag at 81. A timer is then set to begin timing the absolute atrial refractory interval AR1 and the microprocessor goes to sleep.

As previously discussed with respect to FIGS. 5 and 6, the AR1 and extended AR2 intervals are timed out, the input of the atrial amplifier is enabled and AR2 is reset to its nominal value. Prior to timing out the VA interval, the microprocessor is awakened at point 71 of FIG. 3 by the atrial signal 67 of FIG. 2. The microprocessor determines that the AR2 interval has timed out, the DDI flag is not set and the atrial timer has timed out. The microprocessor therefore sets a timer to begin timing the AV interval, disables its input from the atrial amplifier 7, restarts the atrial timer and goes to sleep to await timing out of the AV interval.

When the AV interval times out, the microprocessor wakes up at point 79 of FIG. 4, disables its input from the atrial amplifier, paces the ventricle at 69 of FIG. 2 and sets a timer to begin timing the VA interval. Thereafter it is determined that the atrial timer has not timed out and that the ASKIP flag is not set. The microprocessor therefore clears the previously cleared ASKIP flag at 81 and starts the timing of the atrial refractory intervals in the above-indicated manner.

The timing diagram of FIG. 2 illustrates the operation of the pacing apparatus of the invention in a mode wherein pacing of the atrium is skipped. It should be understood that under other circumstances the atrium will be paced. For example, with reference to FIG. 7, the microprocessor could wake up at 91 when the VA interval has timed out and could then determine at 93 that the atrial timer has timed out and at 101 that the STOPPACE flag has not been set. Under these circumstances the microprocessor will disable its input from the atrial amplifier 7 and will pace the atrium at 105. Thereafter the microprocessor will go to sleep after setting the atrial timer to begin timing its interval and starting a timer to begin timing the AV interval.

FIG. 8 illustrates a flow chart of program steps which will be carried out by the microprocessor if a natural ventricular event is sensed. The logic steps of FIG. 8 were not employed in the discussion of the timing diagram of FIG. 2, because the timing diagram does not include natural ventricular signals.

With reference to FIG. 8, if a natural ventricular signal is sensed, the microprocessor will wake up, start timing the VA interval and will determine at 107 if the atrial timer has timed out. If the atrial timer has completed timing its interval, the microprocessor will clear the ASKIP flag and will then set a timer to time the absolute atrial refractory interval AR1 in the manner previously described with respect to the flow chart of FIG. 4. If the atrial timer at 107 has not timed out, the microprocessor will interrogate the ASKIP flag and, if the flag is set, will set the DDI flag and will thereafter clear the ASKIP flag and start timing the refractory interval AR1. If after interrogating the ASKIP flag it is determined that the flag is not set, the microprocessor will not set the DDI flag, but will instead clear the ASKIP flag and will start timing the AR1 interval. It should be appreciated that the program steps of FIG. 8 for a sensed ventricular event are the same as shown in FIG. 4 for a pace of the ventricle.

Although particular program flow charts have been disclosed to show a preferred embodiment of a software system for operating a microprocessor-controlled pacemaker in accordance with the invention, it should be understood that the disclosed flow charts are not intended to limit the scope of the invention. The invention may be embodied in other specific forms without departing from its spirit or essential characteristics. The present embodiment is, therefore, to be considered in all respects as illustrative and not restrictive. The scope of the invention is indicated by the claims rather than by the foregoing description. All changes which come within the meaning and range of the equivalents of the claims are, therefore, intended to be embraced therein.

We claim:

1. A heart pacemaker, comprising:
   means for sensing atrial and ventricular electrical signals;
   timing means for timing a preselected atrial rate limit interval in response to each sensed atrial signal, the timing of said interval being restarted for each sensed atrial signal;
   means for pacing the ventricle in response to atrial signals sensed when said timing means has timed out said interval;
   means for pacing the ventricle at a preselected demand rate when atrial signals are sensed while said interval is being timed out;
   means for pacing the atrium at a preselected time following a paced or sensed ventricular signal if said interval has timed out before said preselected time; and
   means for skipping a pace of the atrium if said interval is being timed at said preselected time.

2. The heart pacemaker of claim 1, including means for preventing a pace of the ventricle in response to atrial signals occurring in one timing cycle immediately following a previous cycle during which an atrial pace was skipped and during which the ventricle was paced or a ventricular signal was sensed while said atrial rate limit interval was being timed.

3. The heart pacemaker of claim 2, including means for timing an atrial refractory interval from each sensed or paced ventricular signal and means for skipping a pace of the atrium in said one timing cycle when at least one atrial signal is detected following the atrial refractory interval in said one timing cycle.

4. The heart pacemaker of claim 1, including means for operating the pacemaker in the DDI mode for one timing cycle immediately following a previous cycle during which an atrial pace was skipped and during which the ventricle was paced or a ventricular signal was sensed while said atrial rate limit interval was being timed.

5. The heart pacemaker of claims 1 or 2 or 3 or 4, including means for timing an atrial refractory interval following each sensed or paced ventricular signal, said atrial refractory interval including an absolute portion during which atrial signals are not sensed and a relative portion during which atrial signals are sensed but are not applied to initiate a pace of the ventricle, and means for extending said relative portion by a preselected amount for a timing cycle following a timing cycle in which an atrial pace is skipped.

6. A method for operating a dual chamber heart pacemaker comprising the steps of:
   detecting electrical signals in the atrium of the heart;
   restarting the timing of a preselected atrial rate limit interval for each detected atrial signal;
   pacing the atrium in a demand mode at a preselected point in time following each sensed or paced ventricular signal, unless one or more predetermined atrial skip pace conditions occur;
   skipping a pace of the atrium when at least one of said atrial skip pace conditions occurs;
   ignoring for ventricular pacing purposes atrial signals which occur while the atrial rate limit interval is being timed;
   ignoring for ventricular pacing purposes atrial signals which occur in one pacer timing cycle immediately following a previous cycle during which an atrial pace was skipped and a sensed or paced ventricular signal occurred while the atrial rate limit interval was being timed;
   pacing the ventricle at a preselected nominal rate in a demand mode when atrial signals are ignored and therefore cannot initiate a pace of the ventricle; and
   pacing the ventricle in a demand mode in response to each detected atrial signal which is not ignored.

7. The method of claim 6, further including the step of timing an atrial refractory interval following each paced or sensed ventricular signal, said step of skipping a pace of the atrium including:
   skipping a pace of the atrium if the atrial rate limit interval is being timed at said preselected point; and
   skipping a pace of the atrium in said one pacer timing cycle immediately following said previous cycle if at least one atrial signal is detected following said atrial refractory interval in said one cycle.

8. The method of claim 6, further including the step of timing an atrial refractory interval following each paced or sensed ventricular signal, said refractory interval having an absolute portion during which atrial signals are not detected and a relative portion during which atrial signals are detected but are not applied to initiate a pace of the ventricle.

9. The method of claim 8, further including the step of avoiding a pacemaker sustained tachycardia by extending said relative portion of the atrial refractory interval by a preselected amount for the timing cycle following the timing cycle in which an atrial pace is skipped.

10. A heart pacemaker, comprising:
    means for detecting atrial electrical signals in the atrium of the heart;
    atrial timing means for detecting atrial signals which occur at a rate in excess of a preselected atrial rate limit;
    means for detecting electrical signals in the ventricle of the heart;
    means for pacing the ventricle, in the absence of superceding ventricular signals, in response to detected atrial signals which occur at a rate less than or equal to said atrial rate limit, said means for pacing including means for pacing the ventricle, in the absence of superceding ventricular signals, at a preselected rate less than said atrial rate limit in response to detected atrial signals which occur at a rate in excess of said atrial rate limit; and means for pacing the atrium at a preselected time following each detected ventricular signal or ventricular pace, in the absence of superceding atrial signals, unless said pace of the atrium would occur at a rate in excess of said atrial rate limit.

11. A method for operating a dual chamber heart pacemaker, comprising:

sensing atrial signals in the atrium of the heart;

timing a preselected atrial rate limit interval in response to each sensed atrial signal;

restarting the timing of the atrial rate limit interval if an atrial signal is sensed while the atrial rate limit interval is being timed;

pacing the atrium in a demand mode at a preselected time after a sensed or paced ventricular signal, unless the atrial rate limit interval is being timed at said preselected time or a predefined stoppace condition exists at said preselected time;

skipping a pace of the atrium when the atrial rate limit is being timed at said preselected time or when said predefined stoppace condition exists at the preselected time;

pacing the ventricle in a demand mode in response to sensed atrial signals, unless the atrial signals occur while the atrial rate limit interval is being timed or occur in a timing cycle in which a predefined DDI condition exists;

defining said DDI condition as existing in any timing cycle which is preceded by a timing cycle in which a pace of the atrium is skipped and a sensed or paced ventricular signal occurs while the atrial rate limit interval is being timed;

timing an atrial refractory interval after each sensed or paced ventricular event;

timing a preselected VA interval after each sensed or paced ventricular signal; and defining said stoppace condition as existing in any timing cycle in which the DDI condition exists and in which at least one atrial signal is detected during said VA interval and following said atrial refractory interval for the cycle.

12. The method of claim 11, wherein said step of timing an atrial refractory interval includes timing an absolute atrial refractory portion during which atrial signals are not detected and thereafter timing a relative atrial refractory portion during which atrial signals are detected but are not applied to initiate a pace of the ventricle.

13. The method of claim 12, further including the step of avoiding a pacemaker sustained tachycardia by extending said relative portion by a preselected amount for the timing cycle following the timing cycle in which an atrial pace is skipped.

14. A method for operating a dual chamber heart pacemaker, comprising the steps of:

detecting electrical signals in the atrium and ventricle of a heart;

pacing the ventricle in response to atrial signals which occur at a rate less than a predefined atrial rate limit; and pacing the atrium at a predefined time following each paced or sensed ventricular signal, unless an atrial signal is detected within a predefined atrial rate limit interval preceding said time, in which case the atrial pace is skipped.

15. The method of claim 14, including the step of: operating the pacemaker in the DDI mode for one timing cycle following a timing cycle in which an atrial pace is skipped and a sensed or paced ventricular signal occurs within a preceding one of said predefined atrial rate limit intervals.

16. A method for operating a dual chamber pacemaker, comprising the steps of:

detecting atrial and ventricular electrical signals;

pacing the ventricle in response to atrial signals which occur at a rate less than a predefined atrial rate limit;

timing an atrial rate limit interval in response to each atrial signal;

pacing the atrium at a predefined time following each paced or sensed ventricular signal, unless said predefined time occurs when said atrial rate limit interval is being timed, in which case the atrial pace is skipped;

setting an ASKIP flag when an atrial pace is skipped and clearing the flag in response to a succeeding paced or sensed ventricular signal;

setting a DDI flag during one timing cycle following a timing cycle in which the ASKIP flag was set and a sensed or paced ventricular signal occurred while said atrial rate limit interval was being timed;

while said DDI flag is set, preventing atrial signals from initiating a pace of the ventricle;

timing an atrial refractory interval following each paced or sensed ventricular signal;

setting a STOPPACE flag during said one timing cycle when the DDI flag is set and at least one atrial signal occurs after said atrial refractory interval for said one cycle; and skipping an atrial pace for said one timing cycle in which said STOPPACE flag is set.

17. A dual chamber pacemaker for selectively tracking atrial signals and inhibiting pacing of the atrium, comprising:

means for sensing atrial and ventricular electrical signals;

timing means for timing a preselected atrial rate limit interval in response to each sensed atrial signal, the timing of said interval being restarted for each sensed atrial signal;

means for tracking atrial signals sensed when said timing means has timed out said interval and for preventing tracking of atrial signals sensed when said timing means is timing out said interval;

means for pacing the ventricle in response to tracked atrial signals;

means for pacing the atrium at a preselected time following paced or sensed ventricular signals; and means for preventing pacing of the atrium at said preselected time when said timing means is timing out said interval.

18. The pacemaker of claim 17, further including:

means for preventing tracking of atrial signals sensed during one timing cycle following a cycle in which pacing of the atrium was prevented and a paced or sensed ventricular signal occurred while said atrial rate limit interval was being timed.

19. The pacemaker of claim 18, including means for timing an atrial refractory interval from each sensed or paced ventricular signal and means for skipping a pace of the atrium in said one timing cycle when at least one atrial signal is detected following the atrial refractory interval in said one timing cycle.

20. The pacemaker of claim 17, further including means for operating the pacemaker in the DDI mode for one timing cycle immediately following a previous cycle during which an atrial pace was prevented and during which a sensed or paced ventricular signal occurred while said atrial rate limit interval was being timed.

21. The pacemaker of claim 17, including means for pacing the ventricle at a preselected demand rate when atrial signals are not being tracked.

* * * * *